United States Patent
Chen

(10) Patent No.: US 7,176,291 B2
(45) Date of Patent: Feb. 13, 2007

(54) GLYCINE N-METHYLTRANSFERASE MONOCLONAL ANTIBODIES AND METHODS OF USE THEREFOR

(75) Inventor: Yi-Ming A. Chen, Taipei (TW)

(73) Assignee: Gene Research Lab. Co., Ltd., Taipei (TW)

( * ) Notice: Subject to any disclaimer, the term of this patent is extended or adjusted under 35 U.S.C. 154(b) by 620 days.

(21) Appl. No.: 10/301,589

(22) Filed: Nov. 22, 2002

(65) Prior Publication Data

US 2004/0101913 A1     May 27, 2004

(51) Int. Cl.
*C07K 16/40*     (2006.01)
(52) U.S. Cl. .................. 530/388.26; 530/350; 435/338
(58) Field of Classification Search ........... 530/388.26, 530/350; 435/338
See application file for complete search history.

(56) References Cited

FOREIGN PATENT DOCUMENTS

EP     1 422 527 A1 *   5/2004

OTHER PUBLICATIONS

Yeo et al. Proc Natl Acad Sci USA. Jan. 1994; 91: 210-4.*
Tseng et al. Cancer Res. Feb. 1, 2003; 63: 647-54.*
Xie et al. Hybridoma. Oct. 1998; 17 (5): 437-44.*
Chen et al., Genomic Structure, Expression, and Chromosomal Localization of the Human Glycine N-methyltransferase Gene, Genomics, vol. 66, No. 1, pp. 43-47, May 15, 2000.
Liu et al., Characterization of Reduced Expression of Glycine N-methyltransferase in Cancerous Hepatic Tissues Using Two Newly Developed Monoclonal Antibodies, Journal of Biomedical Science, vol. 10, No. 1, pp. 87-97, 2003.
Chen et al., Characterization of Glycine-N-Methyltransferase-Gene Experession in Human Hepatocellular Carcinoma, International Journal of Cancer, vol. 75, No. 5, pp. 787-793, Mar. 2, 1998.

* cited by examiner

*Primary Examiner*—Stephen L. Rawlings
(74) *Attorney, Agent, or Firm*—Rosenberg, Klein & Lee

(57) ABSTRACT

The present invention provides two unique monoclonal antibodies directed against a portion of the human Glycine N-methyltransferase, and methods of use for the monoclonal antibodies in detecting, monitoring and diagnosing malignancies characterized by down-regulation of expression or inappropriate expression of the Glycine N-methyltransferase.

2 Claims, 13 Drawing Sheets

Box plot of GNMT concentration

SEQUENCE LISTING

```
<160> NUMBER OF SEQ ID NOS: 7

<210> SEQ ID NO 1
<211> LENGTH: 27
<212> TYPE: DNA
<213> ORGANISM: Homo Sapiens

<400> SEQUENCE: 1 gaggaattcatggtggacagcgtgtac                                          27

<210> SEQ ID NO 2
<211> LENGTH: 27
<212> TYPE: DNA
<213> ORGANISM: Homo Sapiens

<400> SEQUENCE: 2 gcgctcgaggtctgtcctcttgagcac                                          27

<210> SEQ ID NO 3
```

-continued

```
<211> LENGTH: 8
<212> TYPE: PRT
<213> ORGANISM: Homo Sapiens

<400> SEQUENCE: 3

Gly Asp Phe Lys Pro Tyr Lys Pro
 1               5

<210> SEQ ID NO 4
<211> LENGTH: 7
<212> TYPE: PRT
<213> ORGANISM: Homo Sapiens
<220> FEATURE:
<221> NAME/KEY: protein
<222> LOCATION: 1, 5, 7
<223> OTHER INFORMATION: Any Amino Acid may be used

<400> SEQUENCE: 4

Xaa Phe Lys Pro Xaa Lys Xaa
 1               5

<210> SEQ ID NO 5
<211> LENGTH: 7
<212> TYPE: PRT
<213> ORGANISM: Homo Sapiens
<220> FEATURE:
<221> NAME/KEY: protein
<222> LOCATION: 1, 5, 7
<223> OTHER INFORMATION: Any Amino Acid may be used

<400> SEQUENCE: 5

Xaa Phe Lys Pro Xaa Arg Xaa
 1               5

<210> SEQ ID NO 6
<211> LENGTH: 8
<212> TYPE: PRT
<213> ORGANISM: Homo Sapiens

<400> SEQUENCE: 6

Arg Ser Leu Gly Val Ala Ala Glu
 1               5

<210> SEQ ID NO 7
<211> LENGTH: 6
<212> TYPE: PRT
<213> ORGANISM: Homo Sapiens

<400> SEQUENCE: 7

Ala Leu Gly Thr Ala Ala
 1               5
```

GLYCINE N-METHYLTRANSFERASE MONOCLONAL ANTIBODIES AND METHODS OF USE THEREFOR

FIELD OF THE INVENTION

This invention relates generally to the field of detecting, monitoring and diagnosing malignancies characterized by down-regulation of expression or inappropriate expression of the Glycine N-methyltransferase.

BACKGROUND OF THE INVENTION

Hepatocellular carcinoma (HCC) is one of the world's most common malignancies, causing almost one million deaths annually. HCC has a heterogeneous geographical distribution, which is probably related to differences in prevalence of risk factors among separate world areas. It is one of the most frequently occurring neoplasms in Asia, Africa and the Mediterranean basin.

The incidence of hepatocellular carcinoma is higher in areas with high carrier rates of hepatitis B and C and in patients with haemochromatosis. More than 80% of hepatocellular carcinomas occur in patients with cirrhotic livers. Once viral infection is established, about 10 years are required for patients to develop chronic hepatitis, 20 years to develop cirrhosis, and 30 years to develop carcinoma. In African and Asian countries, aflatoxin produced as a result of contamination of imperfectly stored staple crops by *Apergillus flavus* seems to be an independent risk factor for the development of hepatocellular carcinoma, probably through mutation of the p53 suppressor gene.

In patients with cirrhosis, the diagnosis of hepatocellular carcinoma should be suspected when there is deterioration in liver function, an acute complication (ascites, encephalopathy, variceal bleeding and jaundice) or development of upper abdominal pain and fever. Ultrasonography will identify most tumors, and the presence of a discrete mass within a cirrhotic liver together with an alpha-fetoprotein concentration above 500 ng/ml is diagnostic. Biopsy is unnecessary and should be avoided to reduce the risk of tumor seeding. Surgical resection is the only treatment that can offer a cure. However, because of the local spread of the tumor and the severity of pre-existing cirrhosis, such treatment is feasible in less than 20% of patients. Average operative mortality is 12% in cirrhotic patients, and five-year survival is around 15%.

Patients with cirrhosis and small tumors (5 cm or less) should have liver transplantation. Injection of alcohol or radio frequency ablation can improve survival in patients with small tumors who are unsuitable for transplantation. For larger tumors, trans-arterial embolization with lipiodol and cytotoxic drugs (cisplatin or doxorubicin) may induce tumor necrosis in some patients.

There are no absolute methods for diagnosing or assessing the degree of malignancy of tumors. However, among the methods available, microscopic examination of tissue is still the most reliable method for routine use. In a pathologic study, tumors can be graded by making an approximate assessment of the degree of structural dedifferentiation (anaplasia) based on histological and cytological criteria by microscopically examining sections of the tumors. However, on one hand, some cells may have lost their specific structural characters but still retain differentiated biochemical features, while others may still appear differentiated in structure but have lost many normal function attributes. On the other hand, a tumor is not homogeneous and may contain areas with more than one tumor grade. Therefore, a developed tumor may consist of a mixed population of cells that may differ in structure, function, growth potential, resistance to drugs or X-rays and ability to invade and metastasize. The two limitations reduce the effectiveness of histological examination of tumors. In another aspect, such an examination by sampling specimens is not suitable for investigations on a large scale.

Many attempts to find absolute markers of malignancy have been made. Other attempts to identify tumor-specific or tumor-associated proteins, either by direct measurement or by developing specific antibodies to these proteins, are still being made. They seem to be promising approaches not only in diagnosis but also in providing strategies to destroy cancer cells. A variety of substances wherein the presence or concentrations of the substances in vivo may be indicative for certain cancers have been reported, such as oncofetal antigens, e.g., alpha-fetoprotein; serum proteins, e.g., ferritin; enzymes; polyamines; ectopic hormones; cell markers; receptors or tumor-associated viral antigens. However, the most commonly used method of diagnosis of cancers depends on histology rather than any of the above substances. The lack of any absolute markers is a major deficiency in studying cancer.

Recent observations provide some contemplations in searching for the substances intimately associated with carcinogenesis. Cancer is appreciated as a result of multiple gene aberrations that cause both the activation of oncogenes and inactivation of tumor suppressor genes. Further, the differential expression of those critical genes associated with oncogenes can be reflected at the messenger RNA (mRNA) level in cells. For effectively screening the altered ones of interest amongst a great amount of mRNA, a powerful tool, specifically differential display, has been established to identify and isolate a small subset of genes which are differentially expressed between tumorous and normal cells (Liang et al., Cancer Research 52, 6966–6968, 1992).

SUMMARY OF THE INVENTION

The present invention provides monoclonal antibodies of detecting abnormalities of cells having a decreased level of GNMT. To evaluate the expression of GNMT in cell lines and tissues from hepatocellular carcinoma (HCC) patients, we produced two monoclonal antibodies (mAbs) GRL7 and GRL1, using two recombinant GNMT fusion proteins. The M13 phage peptide display showed that the reactive epitopes of mAbs GRL7 and GRL1 were amino acid residues of human GNMT 10–15 and 272–278, respectively.

The dissociation constant of the binding between GNMT and mAbs was $1.7 \times 10^{-8}$ M for mAb GRL7 and $1.8 \times 10^{-9}$ M for mAb GRL1. Both these mAbs are able to identify GNMT present in normal human and mouse liver tissue using Western blotting (WB) and immunohistochemical staining assay (IHC). In addition, WB with mAb GRL1 showed that neither the 2 hepatoblastoma and nor the 5 HCC cell lines expressed GNMT. An IHC with both mAbs demonstrated that 50% (13/26) of non-tumorous liver tissues and 96% (24/25) of HCC tissues did not express GNMT. Thus we concluded that, the expression of GNMT was down regulated in human HCC.

A quantitative enzyme immunoassay for the measurement of GNMT in human serum was established. Serum samples from 413 healthy people, 90 patients with chronic hepatitis, 20 patients with liver cirrhosis and 22 patients with HCC were used. The results showed that the serum levels of GNMT among these four groups of patients were 11.04±16.24 (healthy people), 7.19±9.25 (chronic hepatitis), 3.14±3.38 (cirrhosis) and 2.19±2.54 ng/ml (HCC), respectively (ANOVA test, p<0.05).

DETAILED DESCRIPTION OF THE PREFERRED EMBODIMENTS

Figure 1A:
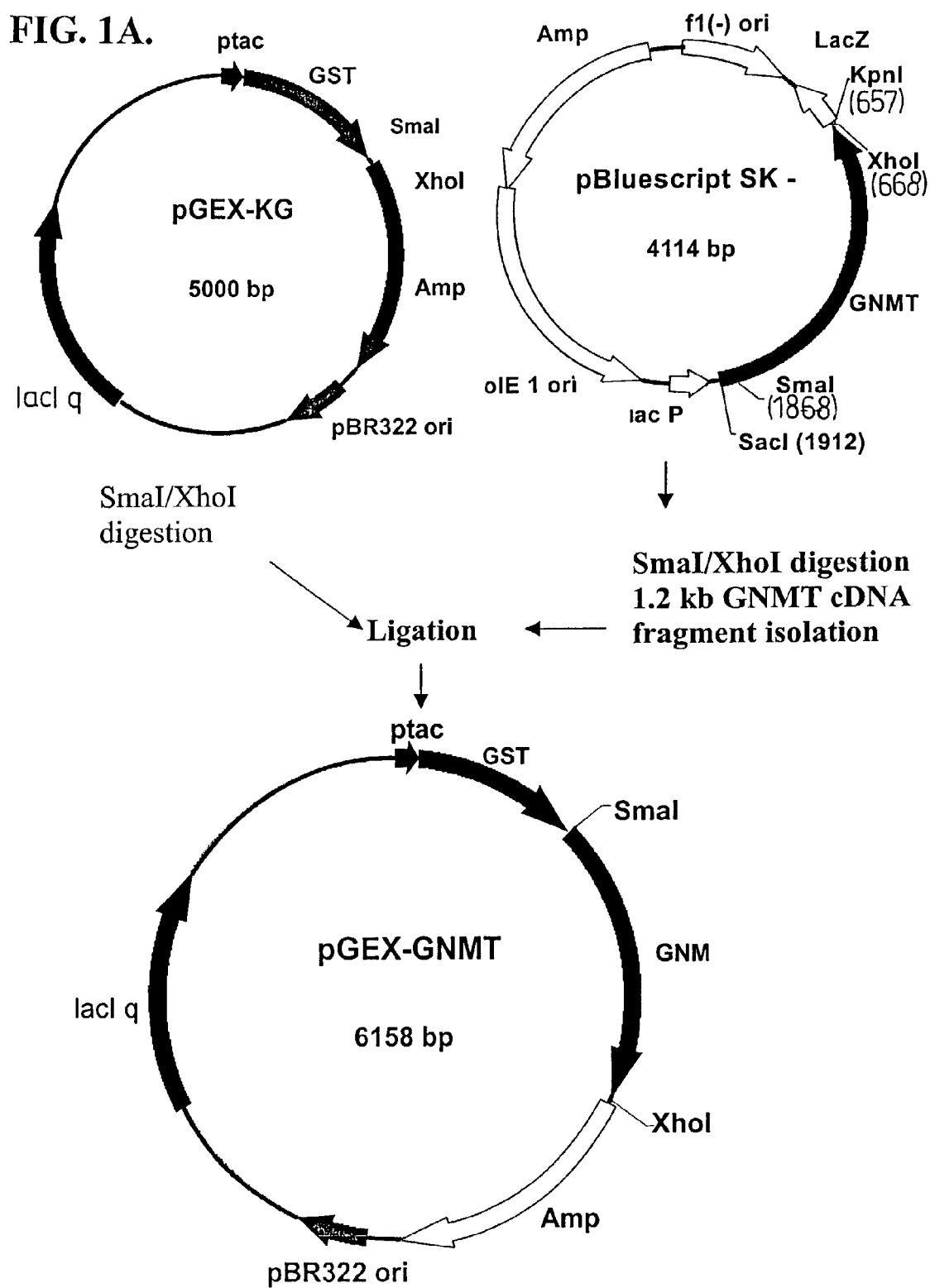
FIG. 1A–1B are construction diagrams of two recombinant GNMT expression plasmids pGEX-GNMT and pGNMT-His.

Glycine N-methyltransferase (GNMT, EC 2.1.1.20) was originally revealed to be an enzyme regulating the ratio of S-adenosylmethionine (SAM) to S-adenosylhomocysteine by catalyzing the synthesis of sarcosine from glycine and SAM [Kerr S J, et. al. 1972, Ogawa H, et. al. 1982]. GNMT is conservative among different animal species [Bork P. et. al. 1992, Chen Y M. et. al. 1998, Lai M C. et. al. 1999b, Ogawa H. et. al. 1993]. In Halophilic Methanoarchaea, GNMT plays a major role in osmoregulation [Lai M C. et. al. 1999a]. In rabbit and rat livers, GNMT comprises 1–3% of the cytosolic proteins, and it has been suggested to play an important role in the metabolism of methionine [Cook R J, et al. 1984, Heady J E, et al.1975, Ogawa H, et. al. 1982].

Previously, through mRNA differential display and northern blot analysis of liver tumors and non-tumorous liver tissue from human hepatocellular carcinoma (HCC) patients, we reported that the expression level of GNMT was diminished in tumorous tissue and HCC cell lines [Chen Y M, et al. 1998]. Subsequently, the human GNMT gene was isolated, sequenced and mapped to chromosome 6p12 [Chen Y M, et al 2000]. Additionally, genotypic analyses of different polymorphisms of the human GNMT gene demonstrated that 36–47% of the genetic markers showed loss of heterozygocity in tumorous tissues of HCC patients [Tseng T L, et al.]. Functional characterization of GNMT showed that GNMT is able to bind benzo(a)pyrene (BaP) and decrease BaP-DNA adduct formation [Chen S Y, et al., Raha A, et al. 1994]. Therefore, GNMT can be classified as a tumor susceptibility gene.

Furthermore, GNMT has been shown to have diverse functions and the ability to compete with the Ah (dioxin) receptor for binding Benzo(a)pyrene (BaP), down-regulating BaP-dependent cytochrome P450 1A1 expression and decreasing BaP-DNA adduct formation [Chen S Y, et al., Krupenko N I, et al.]. That the activity of GNMT is significantly decreased in rat hepatoma has also been shown [Houser W H, et al. 1985]. In addition, a rat hepatoma model induced through N-2- fluorenylacetamide, the GNMT enzyme activity gradually decreased and became undetectable in the liver tumor after 8 months of treatment [Zhang Y J, et al. 1991]. From these studies, we can conclude that the down-regulation of the GNMT gene expression is present in both naturally-occurring and carcinogen-induced liver cancers.

Recently, Mudd et al. reported that two Italian siblings who had mild hepatomegaly and chronic elevation of serum transaminases were diagnosed to have GNMT deficiency [Mudd S H, et al 2001]. Both children had compound heterozygotes of the GNMT gene with missense mutations [Luka Z, et al 2002].

Therefore, the present invention fuirther provides monoclonal antibodies for detecting, monitoring and diagnosing the decreased level of GNMT by immunohistochemistry and EIA methods.

All of the documents or publications recited in the text are incorporated herein by reference.

That the GNMT gene is differentially expressed between normal and tumorous cells with a significant distinction is surprisingly found in the present invention. An objective of the present invention is to provide a method of detecting abnormalities of cells by determining the relative levels of gene expression of GNMT. Furthermore, another objective of the present invention is to provide a method of correcting the abnormalities of cells by delivering GNMT into the abnormal cells.

In this invention, we used monoclonal antibodies against GNMT to establish a sensitive method to monitor the correlation between the GNMT in serum or plasma and the pathogenesis of HCC formation. The polyclonal antibodies against human GNMT as capture antibody were used to capture the human GNMT in serum or plasma, and further analyze by monoclonal antibody GRL1 as indicating antibody. We setup a quantitative enzyme immunoassay to measure the quantity of human GNMT in blood.

Additionally, the monoclonal antibodies posses immunogenic epitopes that can be used as a reference to make synthetic peptides for the generation of antisera or for the production of other diagnostic assay.

Further details of this invention are illustrated in the following examples.

EXAMPLES

Example 1

Construction of GNMT Expression Vector 1.1. Construction of the pGEX-GNMT

For the construction of the pGEX-GNMT, a full-length GNMT cDNA fragment was cleaved from pBluescript-GNMT-9-1-2 phagemid DNA [Chen Y M, et al. 1998] by using SmaI and SalI restriction enzymes (STRATAGENE™, La jolla, Calif., USA). This 1.2-kb DNA fragment was ligated to a vector, pGEX-KG [Guan K L, et al. 1991] that had previously been digested with SmaI and XhoI.

1.2. Construction of the pGNMT-His

Figure 1B:
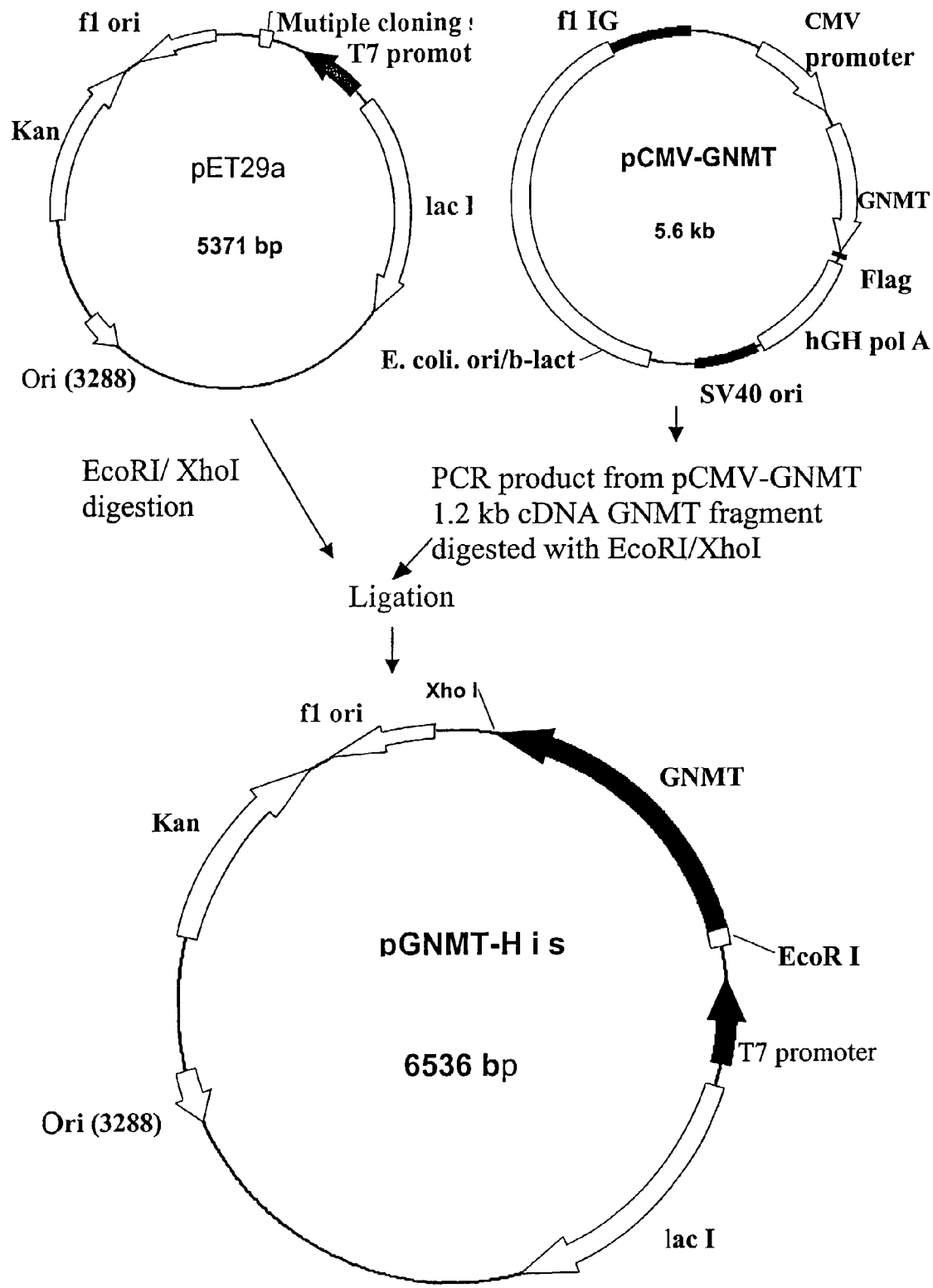
Figure 2A:
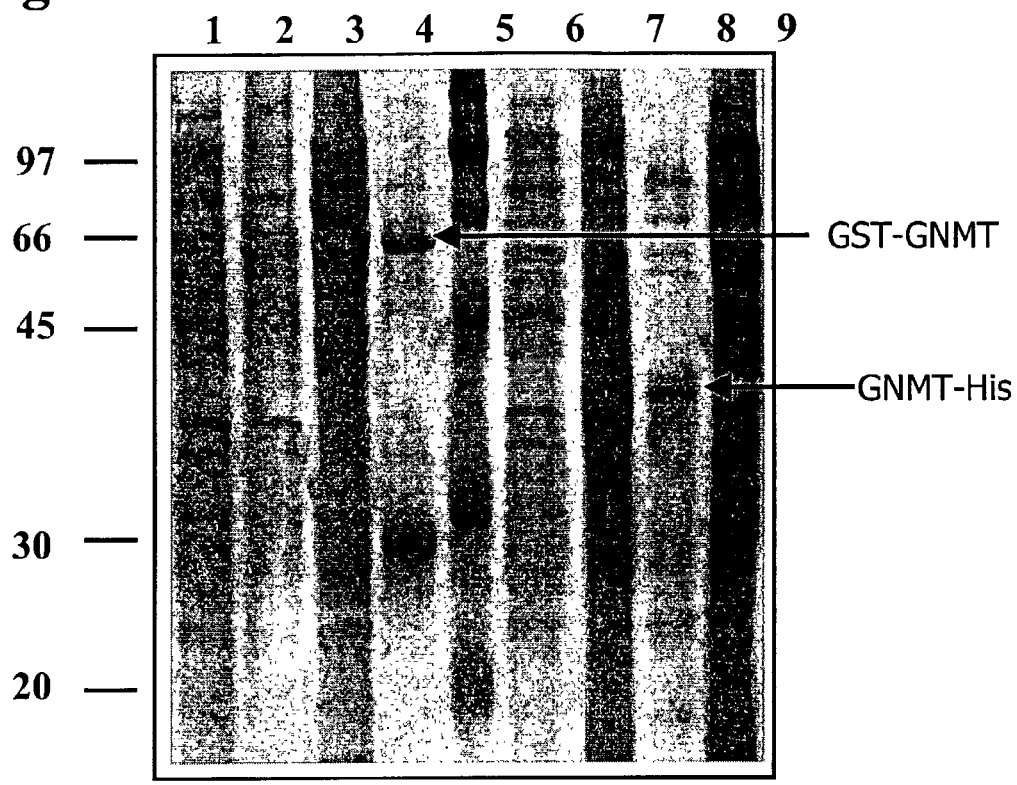
FIG. 2A–2D are electrophoresis results showing identification of recombinant and native forms of GNMT with mAbs GRL1 and GRL7. Panel A: Coomassie Brilliant Blue R250 staining of a SDS-polyacrylamide gel containing lysates from E. coli [JM109] harboring pGEX-GNMT, or [BL21] harboring pGNMT-His before (lanes 1, 6) and after (lanes 2, 7) IPTG induction. The unbound (lanes 3, 9) and the eluent of the bound fractions (lanes 4, 8) from the glutathione agarose bead and nickel affinity column for His tag purification procedure were also run in the lane 4 and lane 8, respectively. Panel B: WB of mAbs to strips with GST-GNMT and GNMT-His recombinant proteins. Strips were reactive with a pre-immunized rabbit serum (lane 1), a rabbit anti-GST-GNMT antiserum-R4 (lane 2), a normal mouse serum (lane 3), mAb GRL1 (lane 4) and mAb GRL7 (lane 5). These strips used the indirect method, and exhibited color by substrate 3-3' diaminobenzidine. Panel C: WB assays on strips with cell lysates from 293T cells transfected with pCMV-GNMT plasmid DNA. Panel D: WB assays on strips with GST and GNMT. Antibodies used in the panels C and D: lane 1, pre-immunized rabbit serum; lane 2, R4; lane 3, normal mouse serum; lane 4, mAb GRL7; and lane 5, mAb GRL1. Molecular weight markers were labeled at the left margin (in kd) of each panel except panel A (lane 5).
Figure 2B:
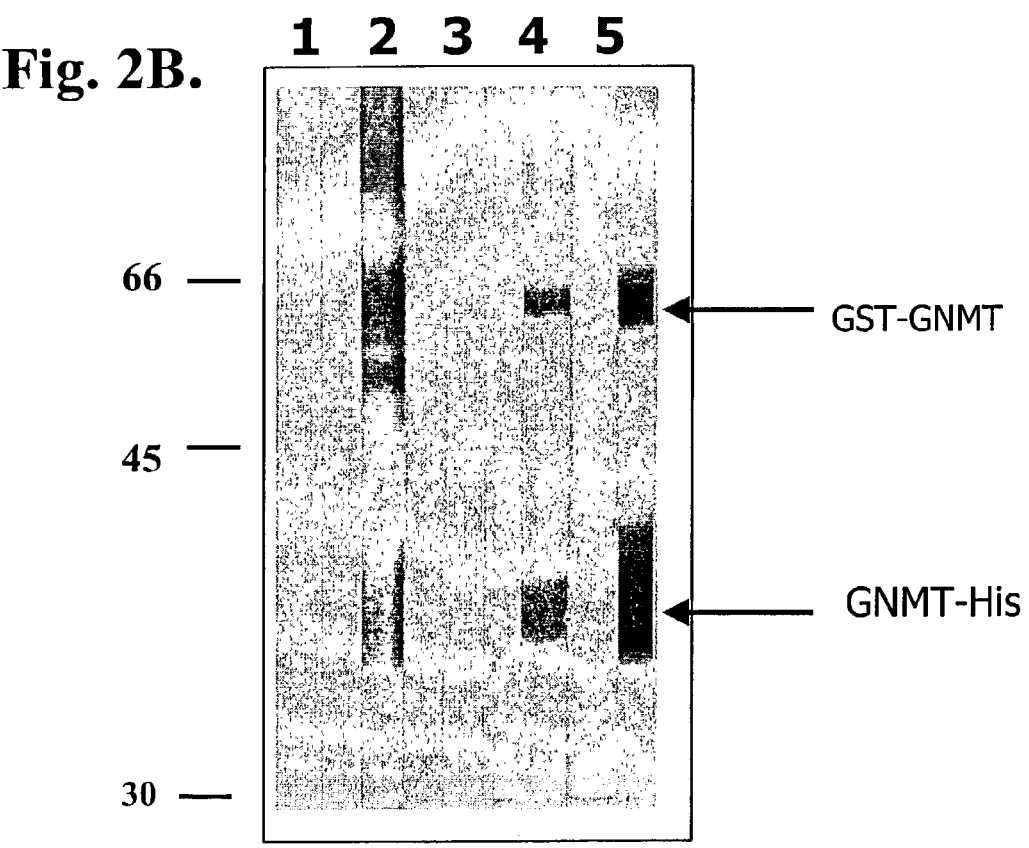
Figure 2C:
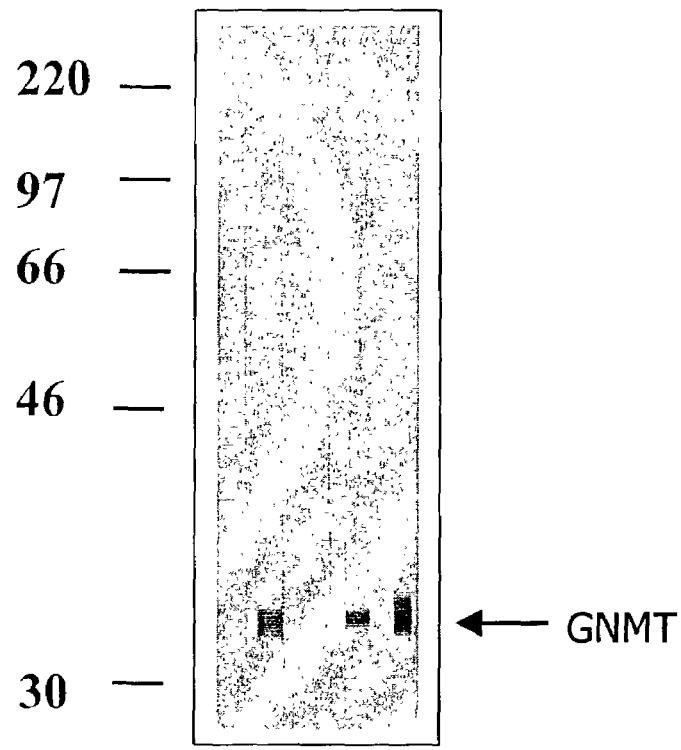
Figure 2D:
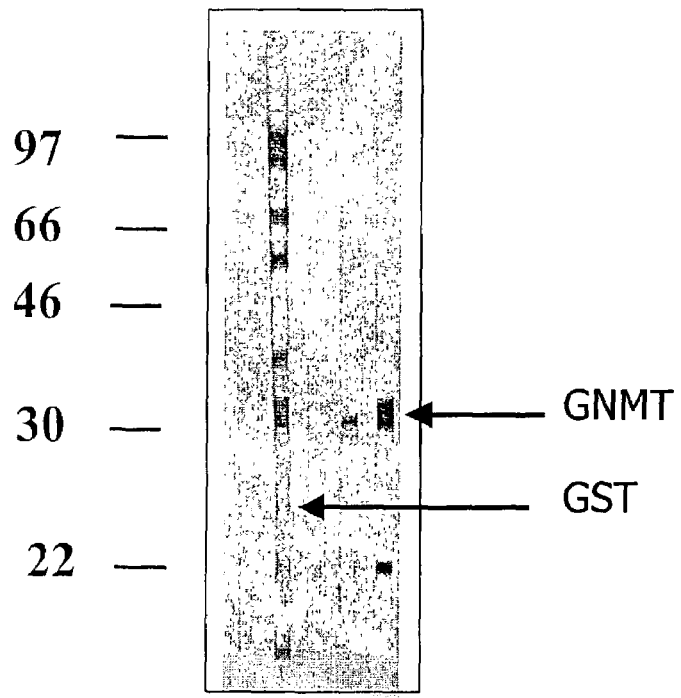

For the construction of pGNMT-His, as shown in FIG. 1B, plasmid pCMV-GNMT [Chen S Y, et al.] was used as a template in the polymerase chain reaction (PCR). A 1.2-kb DNA fragment containing GNMT cDNA sequence and restriction enzyme sites on both ends was amplified. Twenty- PCR cycles were performed in a DNA Thermal Cycler (PERKIN-ELMER CETUS™ Foster City, Calif., USA) using their AMPLITAQ GOLD™ TAQ DNA polymerase. The upstream primer (5'-GAGGAATTCATGGTGGACAGCGTGTAC) SEQ ID NO: #1 consisted of a 3-bp "clamp" (GCG) at the 5' end, followed by one restriction enzyme site (EcoRI) and a GNMT cDNA sequence. The downstream primer (5'-GCGCTCGAGGTCTGTCCTCTTGAGCAC) SEQ ID NO: #2 containing a similar structural sequence motif as the upstream primer, except that it consisted of negative strand sequences from the terminal region of GNMT cDNA and a different restriction enzyme site (XhoI). After the PCR, the 1.2-kb DNA fragment was gel-purified, digested with EcoRI and XhoI and ligated to a vector pET29a (NOVAGEN™, Inc., Madison, Wis., USA) that had been digested with the same pair of restriction enzymes. The DNA sequences of both plasmids were confirmed by automated DNA sequencing using an ABI Prism dye terminator cycle sequencing core kit (PERKIN-ELMER CETUS™).

The *Escherichia coli* strain JM109 or BL21 was used as the recipient in the transformation and expression experiments for pGST-GNMT. In addition, plasmid pGEX-KG [Guan K L, et al. 1991] was used for the induction and purification of glutathione S-transferase (GST) protein that served as a parallel control in the enzyme immunoassay.

1.3. Expression and Purification of Different GNMT Recombinant Proteins

All the GST, GST-GNMT and GNMT-His recombinant proteins (RPs) were induced in JM109 or BL21 cells through isopropyl-beta-D-thiogalactopyranoside (IPTG). The transformants of GST-GNMT and His-GNMT had induction optical densities of 0.6–0.7, 0.7–0.8, respectively. Their respective induction times were 3.5 hours and 1 hour. Both the GST and GST-GNMT RPs were purified using glutathione-Sepharose 4B beads (Pharmacia, Uppsala, Sweden), as described by Guan et al. [Guan K L, et al. 1991]. The GNMT-His RP was purified using $Ni^{2+}$-charged histidine (His)-bind resin column according to the procedures provided by the manufacturer (Novagen). The bound GST-GNMT-RP was eluted from the glutathione-Sepharose 4B beads using a 5 mM reduced glutathione buffer. The thrombin digestion method was used to purify GNMT RP from the bead-bound GST-GNMT fusion protein. Concentrations of the RPs were measured using the Pierce BCA protein assay reagent (Pierce, Rockford, Ill., USA) and purity was analyzed by running the samples on a 12.5% SDS-polyacrylamide mini-gel (Bio-Rad Laboratories, Richmond, Calif., USA).

1.4. Production of a Rabbit anti-GNMT Antiserum

To raise rabbit antibodies against GNMT, purified GST-GNMT RP was mixed with Freund complete (for the initial immunization) or incomplete (for the booster injections) adjuvant (Sigma Co., St. Louis, Mo., USA) and the resultant mixture was used as an immunogen to inoculate 8-week-old NZW rabbits (150–200 μg RP per rabbit) subcutaneously. Rabbits received booster injections every 3 weeks after the initial injection with additional doses of the same RP. Rabbit sera were collected before the immunization and 1 week after each injection. All sera were heat inactivated at 56° C. for 30 min and stored at −20° C.

1.5. Preparation of Monoclonal Antibodies Against GNMT

Murine mAbs were produced by a hybridoma technique commonly used in our laboratory. Briefly, BALB/c mice were immunized with purified GST-GNMT and GNMT-His RPs mixed with complete (for primary immunization) or incomplete (for booster injections) Freund adjuvant (SIGMA™), at 10 days intervals by intra-peritoneal (i.p.) injection with a dosage of about 25 μg of RP per inoculum. Serum samples were collected from the tail vein before the immunization and 1 week after each injection. Three days after the last intravenous injection (i.v.) of RP, a fusion of the splenocytes of immunized mice with mouse myeloma cells NS1 (AMERICAN TYPE CULTURE COLLECTION™, Rockville, Md.) was performed with PEG1500 (ROCHE DIAGNOSTICS GmbH™, Mannheim, Germany), and cultured on ninety-six-well plates [Chu T M, et al 1993]. The culture supernatants were screened using the GST/GNMT EIA and also with WB strips blotted with GST, GST-GNMT, GNMT-His RP. Selected hybridoma cells were expanded and cloned at least twice by limiting dilution, and grown as ascitic tumors in 0.5 ml pristine (SIGMA™)-primed BALB/c mice. MAbs were purified and concentrated in Protein-A antibody purification kits (PRO-CHEM™ Inc. Acton, Mass., USA.) and Centricon Plus-80 columns (MILLIPORE™, Bedford, Mass., USA).

1.6 Cell Lines and Cell Culture
Deposit Accession Number: PTA-5319
Date of Deposit: 14 Jul. 2003
Description: B Lymphocyte, Hybridoma, Mus Musculus: GRL1
Name/Address of Depository: American Type Culture Collection™ ("ATCC")
10801 University Boulevard
Manassas, Va. 20110-2209
Deposit Accession Number: PTA-5195
Date of Deposit: 14 May 2003
Description: B Lymphocyte. Hybridoma, Mus Musculus: GRL7
Name/Address of Depository: American Type Culture Collection™ ("ATCC")
10801 University Boulevard
Manassas. Va. 20110-2209

Hybridoma Cell Lines and Culture

The hybridoma cell line was cultured in RPMI 1640 medium (GIBCO-BRL™, Gathersburg, Md., USA) supplemented with 10% heated-inactivated fetal calf serum, 2 mM L-glutamine, penicillin (100 IU/ml) and streptomycin (100 IU/ml) as described in [Chu T M, et al. 1993].

1.7. Hepatoblastoma and HCC Cell Lines and Culture

Two human hepatoblastoma cell lines-HepG2 [Aden D P, et al 1979, Javitt N B.1990], Huh 6 [Nakabayashi H, et al.1982], and five HCC lines Huh 7 [Nakabayashi H, et al. 1982], HA22T [Chang C, et al 1983], PLC/PRF/5 [Luka Z, et al 2002], Hep3B and Sk-Hep1 [Aden D P, et al. 1979, Fogh J, et al. 1976, Fogh J, et al. 1977] were used in this study. These cells were cultured in Dulbecco's modified Eagle's medium (GIBCO-BRL™ Grand Island, N.Y.) with 10% heat-inactivated fetal bovine serum (HYCLONE™, Logan, Utah), penicillin (100 U per ml), streptomycin (100 μg per ml), nonessential amino acids (0.1 mM), fungizone (2.5 mg per ml), and L-glutamine (2 mM) in a humidified incubator with 5% $CO_2$.

1.8. Enzyme Immunoassay (EIA) for Screening of GNMT mAbs

EIA was used to monitor the antibody titers of the immunized animals and to screen for mAbs in the supernatant of different hybridomas. Ninety-six-well plates, coated with either GST-GNMT or GNMT-His RP at a concentration of 1 μg per ml (100 μl per well) were used. Antibody titers of either rabbit or mouse serum were determined at a serial 10-fold dilution. To screen the hybridomas from animals immunized with GST-GNMT RP, EIA plates coated with GST were also used to rule out those mAbs reactive with the GST. Additionally, to screen the hybridomas from animals immunized with GNMT-His RP, GST-GNMT-coated plates were used to confirm those positive clones screened by the GNMT-His-coated plates. A rabbit anti-GNMT antiserum (R4) and multiple mouse anti-GNMT anti-sera were used as the positive controls in the EIA. Details of the procedures have been described previously [Chen Y M, et al. 1991].

1.9. Determination of IgG Concentrations of mAbs by IgG EIA Quantitation Kits

The concentrations of mAbs were determined by mouse IgG EIA quantitation kits (Bethyl laboratory, Montgomery, Tex., USA) and the immunoglobulin concentrations were analyzed using EIA EIX808 readers with 4-parameter logistic regression (BIO-TEK™ instruments, Winooski Vt., USA). All the isotyping and light chain determination was done using mouse immunoglobulin isotyping ELISA kits (BD Biosciences PHARMINGEN™, San Diego, Calif., USA).

Example 2

Characterization of Monoclonal Antibodies 2.1. Epitope Mapping with M13 Phage Peptide Display The antibodies were diluted with 0.1M $NaHCO_3$ (pH 8.6) to a concentration of 100 μg/ml, and added to 5 ml sterile polystyrene Petri dishes. After coating overnight at 4° C. in a humidified container, the plates were blocked with blocking buffer (0.1 M $NaHCO_3$ pH 8.6, 5 mg/ml BSA, 0.02% $NaN_3$, with a sterilized filter, stored at 4° C.) and incubated for at least 1 hour at 4° C. M13 phages displaying random heptapeptides at the N-terminus of its minor coat protein (pIII) were used (Ph.D.-7TM Phage Display Peptide Library, New England Biolabs Inc. Beverly, Mass., USA). The selection of specifically bound phages was done according to the manufacturer's instructions. The 5'-end nucleotides of gene III from the chosen phages were sequenced and then encoded peptides were deduced as show in table 1 [Cortese R, et al 1996].

TABLE 1

| A. GRL1 | | | | | | | |
|---|---|---|---|---|---|---|---|
| GNMT sequence | $^{271}$G | D | F | K | P | Y | K | $P^{278}$ |
| M13 phage display #1I | K | T | P | — | W | — | | |
| #2 | | H | — | — | — | H | — | V |
| #3 | | H | — | — | — | H | — | V |
| #4 | | H | — | — | — | F | R | L |
| #5 | | Y | Y | — | — | — | — | — |
| #6 | | — | Y | — | — | F | R | A |
| #7 | W | — | — | — | — | — | R | |
| #8 | T | E | — | — | — | — | R | |
| #9 | | E | — | — | — | F | — | Y |
| Consensus Sequence: | | X | F | K | P | X | K/R | X |

| B. GRL7 | | | | | | |
|---|---|---|---|---|---|---|
| GNMT sequence | R | $S^{10}$ | L | G | V | A | $A^{15}$ |
| M13 phage display #1 | A | — | — | T | — | — | F |
| #2 | | R | W | — | T | — | — | F |
| #3 | | T | W | — | T | — | — | W |
| #4 | Q | A | — | — | I | — | — |
| #5 | K | T | — | — | Y | — | — |
| #6 | | A | M | — | — | — | F | R |
| Consensus Sequence: | | A | L | G | T | A | A |

2.2. Coupling of GNMT to the Biosensor Surface

Figure 3A:
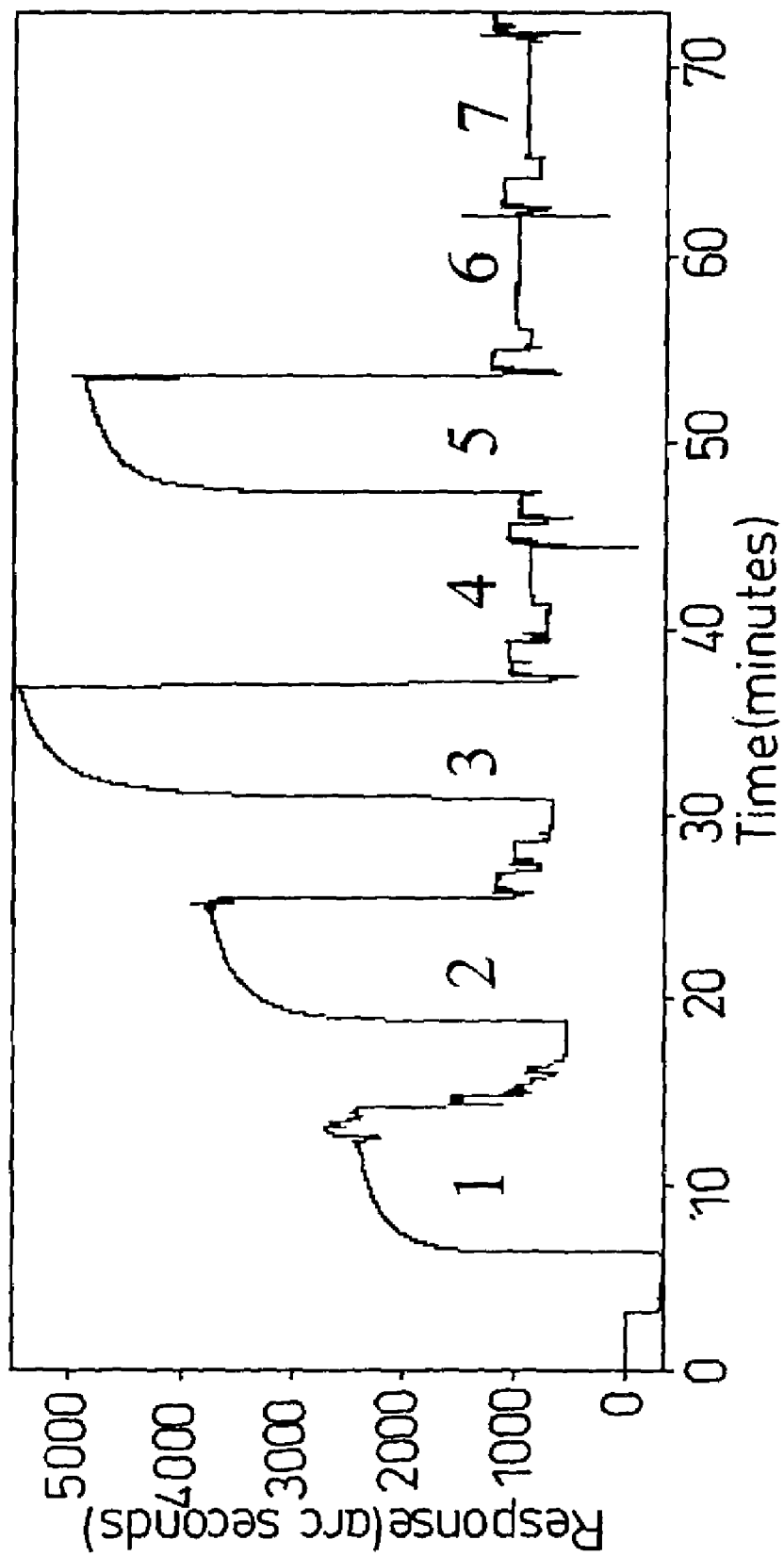
FIG. 3A–3B are response plots of GNMT coupled to a cuvette A. Test of couple pH sodium acetate buffer condition of GNMT: 1. pH 4, 2. pH 4.5, 3. and 5. pH 5.0, 4. and 6. pH 5.5, 7. pH 6. B. Coupling reaction of GNMT: stage 1. PBST base line, 2. add EDC/NHS 200 µl 3×6 min, 3. PBST wash 3×, 4. pH 5.0 sodium acetate buffer 200 µl, 5.50 µl GNMT (9 µg)+150 µl pH 5.0 sodium acetate buffer for 5 min, 6. 1M ethanolamin pH8.5 200 µl for 5 min to stop the coupling reaction, 7. two cycles of regeneration reactions by 10 mM HCl and PBST 3× wash.
Figure 3B:
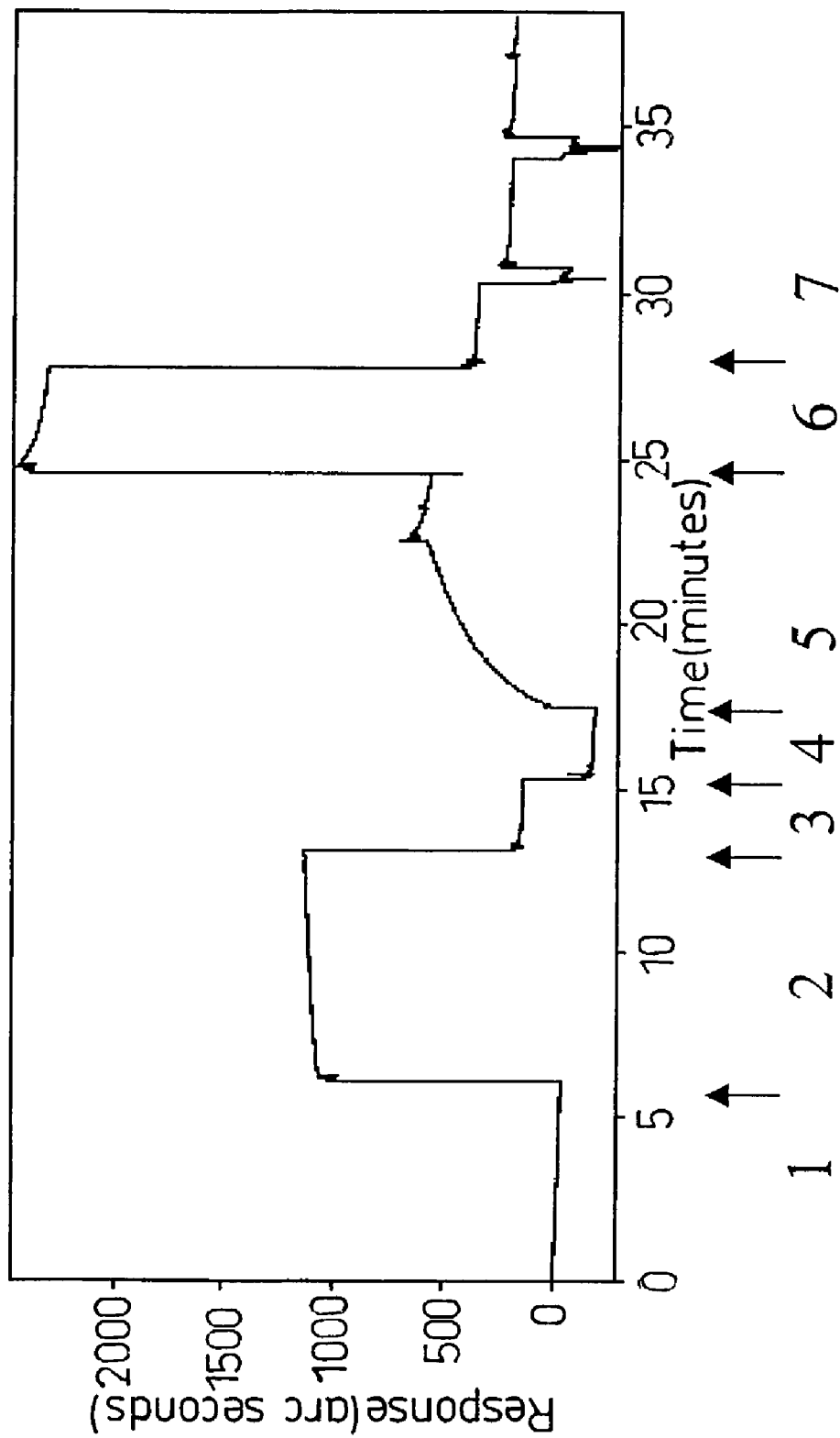

The carboxymethyl dextran (CMD) sample cuvettes were purchased from Thermo Labsystems. In initial experiments, coating conditions were optimized with regards to the pH. The surface was equilibrated in 10 mM sodium acetate buffers, with pH ranging from 4 to 6 in 0.5 unit steps for 6 min. Samples of 9 µg human GNMT RP (thrombin-cleaved) in the same buffer were then added to the cuvette. To test, optimized pH conditions were created. The binding of the RP to the cuvette, which is due to electrostatic attraction between the negative charged carboxyl groups on the dextran and the positively charged protein, was performed for 6 min. Optimized response occurred under a pH 5.0 in a 10 mM acetate buffer as shown on FIG. 3A. Nine µg GNMT RP cleaved by thrombin were used to couple the CMD surface cuvette in 10 mM sodium acetate buffer under optimized pH by a 1-ethyl-3-(3-dimethylaminopropyl) carbodiimide (EDC)/N-hydroxysuccinimide (NHS) method shown in FIG. 3B.

Figure 4A:
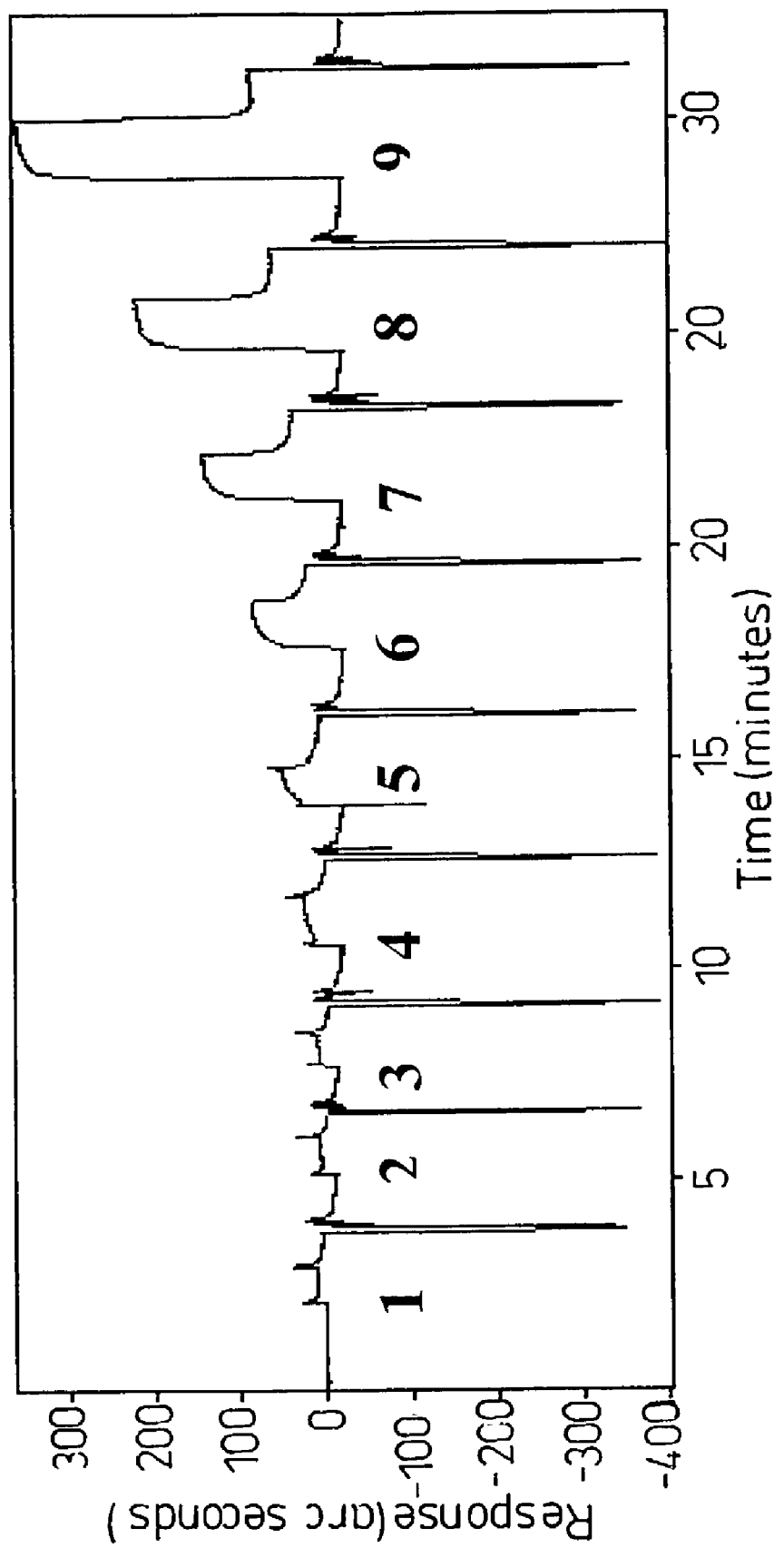
FIG. 4A–4B are response plots of mAbs GRL1 and GRL7 to a cuvette coupled with recombinant GNMT. A two-fold dilution in PBST of 200 µl culture supernatant was added to the cuvette, and the response was measured by IAsys control software version 3.01. The resulting dissociation constant of these two mAbs was calculated by FAST fit. The immunoglobulin concentration of GRL1: A. (1). $4\times10^{-11}$, (2). $8\times10^{-11}$, (3). $1.6\times10^{-10}$, (4). $3.2\times10^{-10}$, (5). $6.3\times10^{-10}$, (6). $1.3\times10^{-9}$, (7). $2.5\times10^{-9}$, (8). $5.1\times10^{-9}$, (9). $1.0\times10^{-8}$ M; The immunoglobulin concentration of GRL7: B. (1). $4.7\times10^{-11}$, (2). $9.4\times10^{-11}$, (3). $1.9\times10^{-10}$, (4). $3.8\times10^{-10}$, (5). $7.5\times10^{-10}$, (6). $1.5\times10^{-9}$, (7). $3\times10^{-9}$, (8). $6\times10^{-9}$, (9). $1.2\times10^{-8}$ M
Figure 4B:
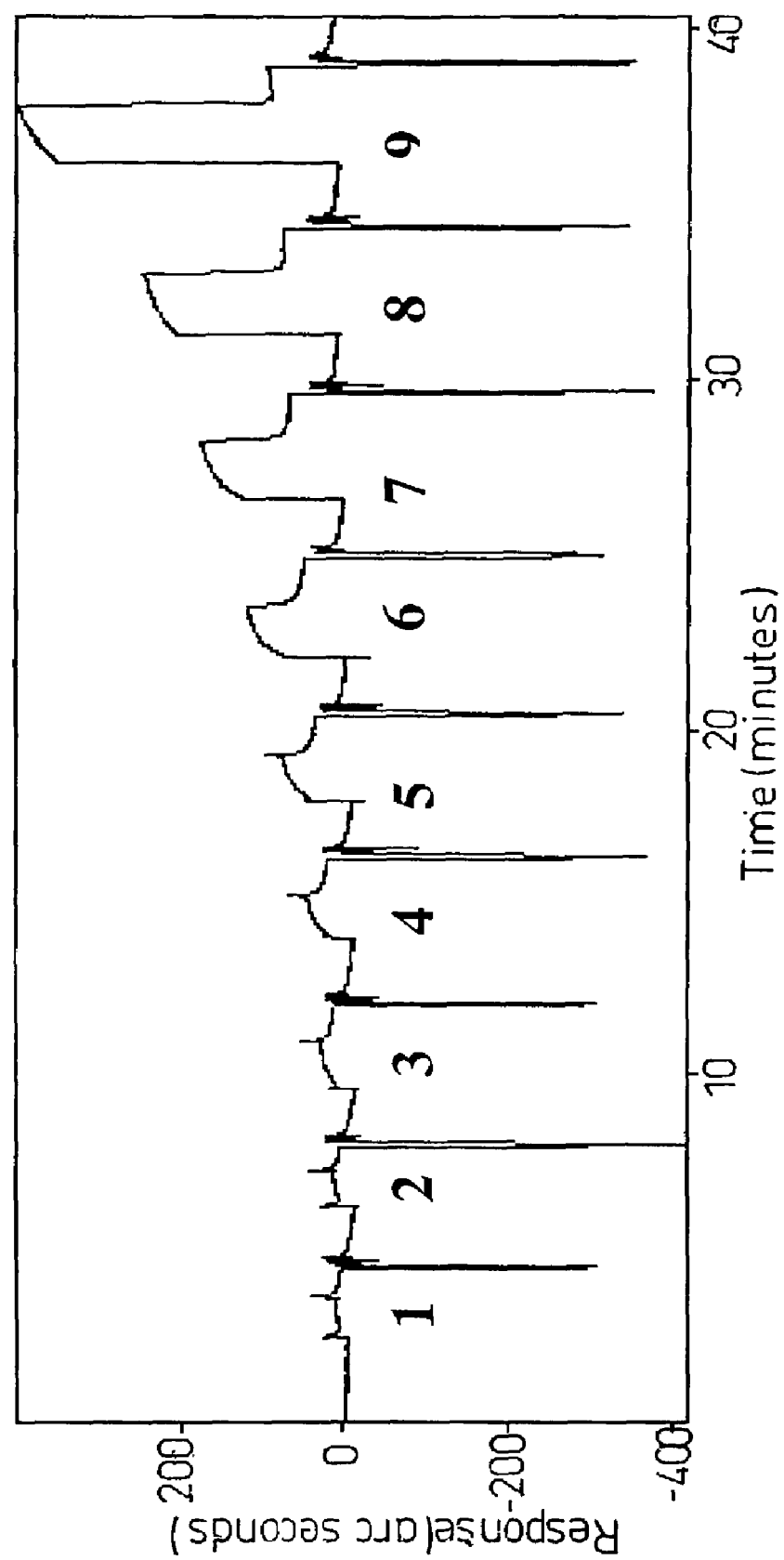

2.3. Determination of the Dissociation Constants using IAsys Affinity Sensor 2.3.1. Determination of the Kd of mAbs Following the immobilization of GNMT, a PBST/Tween 20 (PBST) baseline was established, and the stirring rate in the cuvette was kept constant, 100 rpm for all reactions. A series of 2 fold dilutions (in 200 µl PBST) of mAb from culture supernatant were added to the cuvette, and responses were measured by IAsys control software 3.01 as shown in FIG. 4A,B. Kinetic analysis of the binding data was undertaken using the curve-fitting kinetic analysis software FAST fit (Thermo Labsystems, Affinity Sensors Division, Cambridge, UK) designed for the IAsys, and Kd, determined as previously described [Morgan C L, et al. 1998].

Example 3

3.1. Western Blot Assay (WB)

Figure 5A:
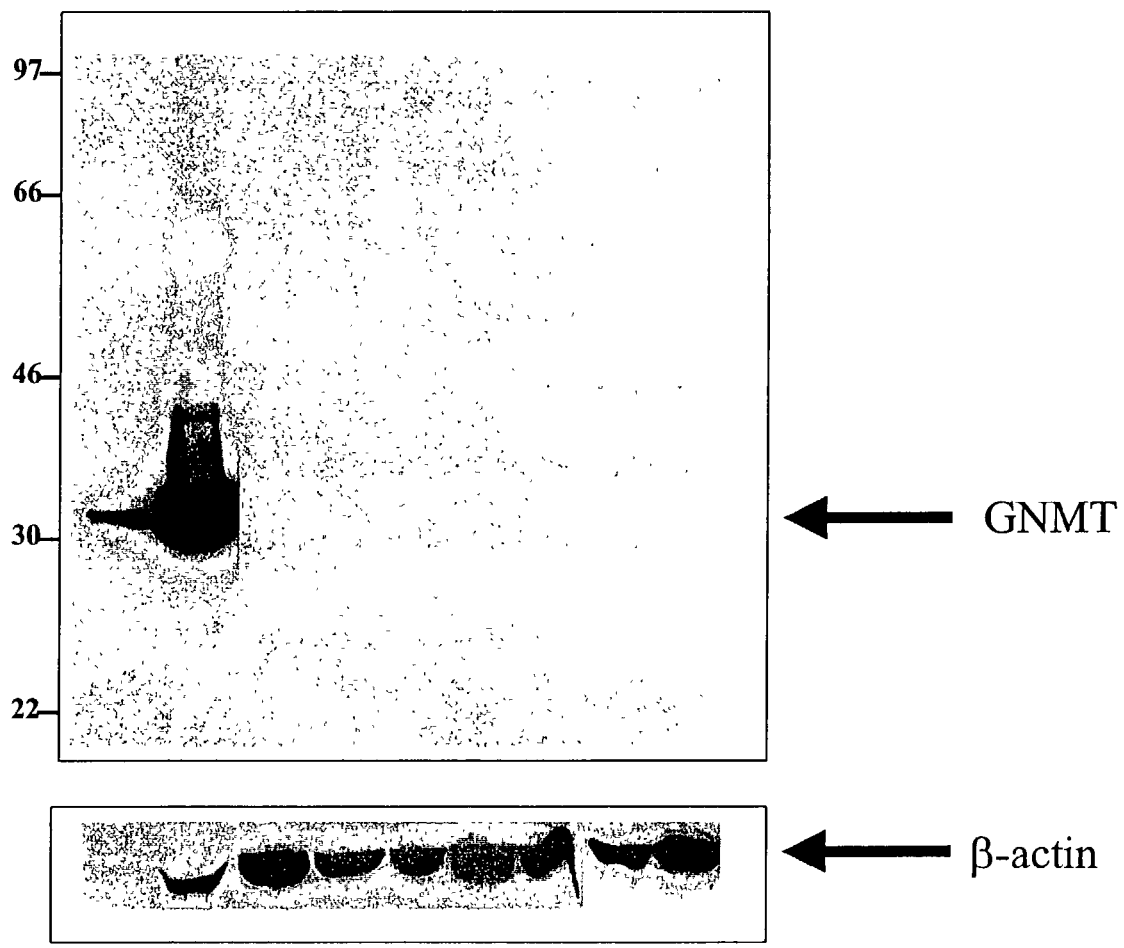
FIG. 5A–5B are the results of western blot analysis of the presence of GNMT in human liver, mouse liver, hepatoblastoma (HepG2 and Huh 6) and hepatocellular carcinoma cell lines (PLC/PRF/5, Huh 7, HA22T, Hep3B and Sk-Hep 1) with mAb GRL1 (panel A) or GRL7(panel B). Lane 1, non-tumorous tissue from a hepatoma patient; lane 2, liver from a C57/BL mouse; lane 3, HepG2; lane 4, PLC/PRF/5; lane 5, Huh 6; lane 6, Huh 7; lane 7, HA22T; lane 8, Hep3B; and lane 9, Sk-Hep1. Lower panels were the same lane with anti-beta actin antibody. Molecular weight markers were labeled at the left margin (in kd) of each panel.
Figure 5B:
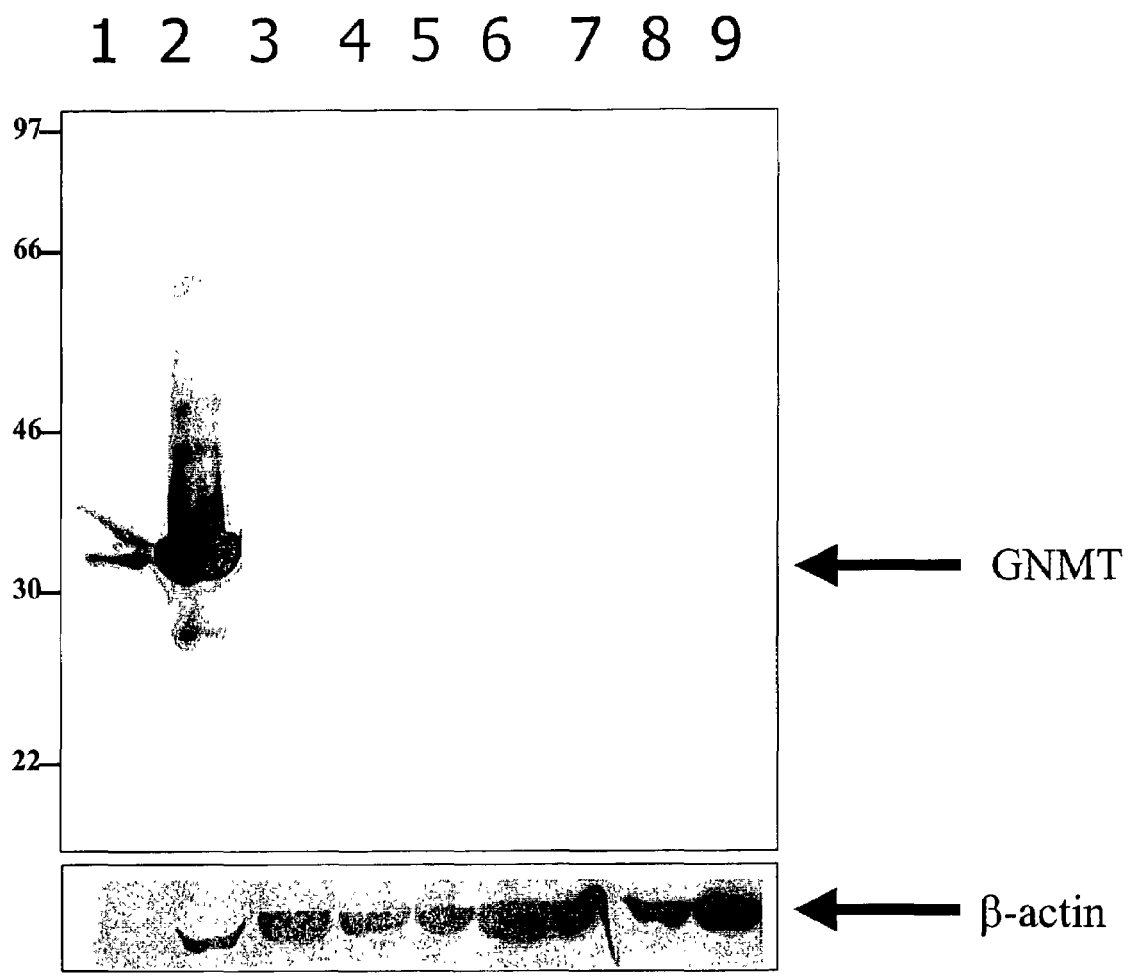

WB was used for the confirmation of the mAbs against GNMT. Three RPs-GST-GNMT (58 kd in size), His-GNMT (37.4 kd in size), GST (26 kd in size), as well as human and mouse liver proteins were used as the antigens in the WB. In the strip experiment and after incubation of mAbs GRL1, GRL7 and R4, normal mouse and pre-immune rabbit serum washed the strip and reacted with horseradish peroxidase-conjugated goat-anti-murine immunoglobulin (SIGMA™). Finally, the resultant serum was developed with 3,3'-diaminobenzidine tetrahydrochloride solution (ZYMED™ Laboratories Inc. Calif., USA. (GST, GST-GNMT, GNMT-His RP)). In the experiment of nitrocellulose membrane and after incubation of mAbs GRL1 and GRL7, anti-β actin (Sigma) washed the membrane and reacted with horseradish peroxidase-conjugated goat-anti-murine immunoglobulin (Sigma) and was finally developed with ECL reagent (AMERSHAN™) as described previously [Chen Y M, et al. 1988]. The results were shown in FIG. 5A, B.

3.2. Immunohistochemistry by Antibodies Against GNMT

Figure 6:
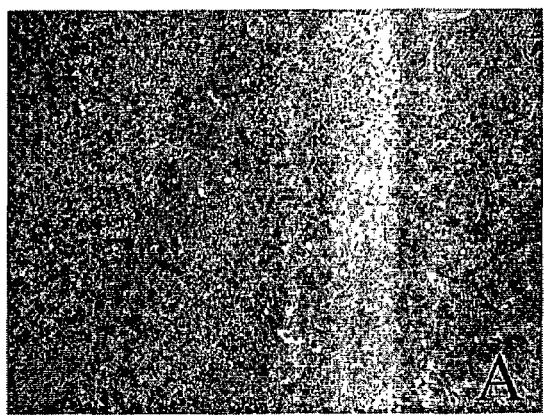
FIG. 6A–6D are the results of immunohistochemical analysis of the GNMT expression using mAb GRL7 or GRL1 in the paraffin-fixed liver tissue sections from two HCC patients. The sections were exposed to mAb GRL7 at 1:25 dilution (panels A, B) or mAB GRL1 at 1:100 dilution (panels C, D) and visualized by a labeled streptavidin-biotin method. Panels A (non-tumorous) and B (tumor tissue) were from an HCC patient-H126 (100-fold magnification). Panels C (non-tumorous) and D (tumor tissue) were from another HCC-patient-H146 (400-fold magnification).
Figure 6:
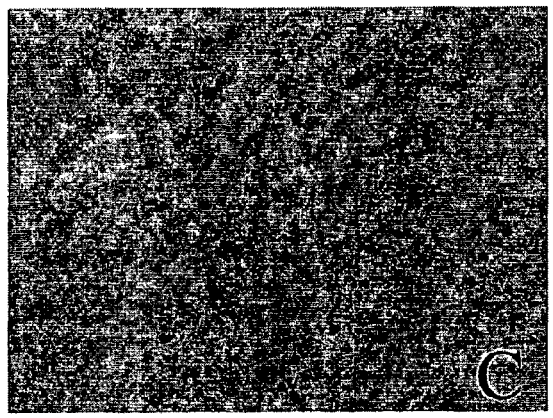
Figure 6:
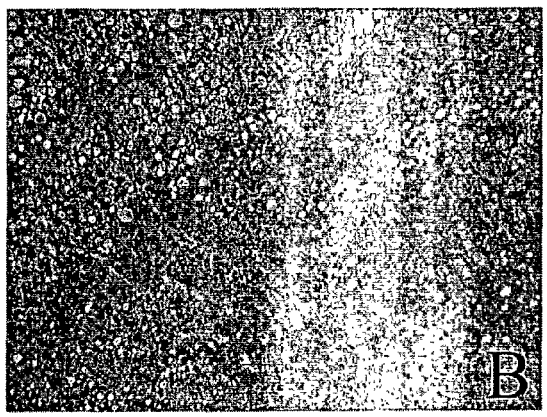
Figure 6:
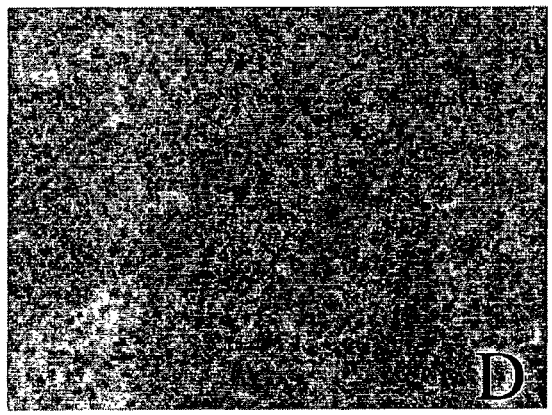

Two sets of tumorous and non-tumorous liver tissue from HCC patients were used for the immunohistochemical procedures with mAbs and R4. The first set included 13 non-tumorous and 9 tumorous tissues (7 pairs) and the second set included 13 non-tumorous and 16 tumorous tissues (9 pairs). All the cancerous and non-cancerous tissue specimens were confirmed by pathologic examination and shown in table 2 A, B. The tissue blocks fixed in paraffin were sliced into 6-µm-thick sections, de-paraffinized and immersed in a 3% solution of hydrogen peroxide in distilled water for 5 min to abolish the endogenous peroxidase reaction. Primary antibodies, mAb GRL1 (1:100 dilution of the ascites) or mAb GRL7 (1:25 dilution of the ascites) or R4 (1:200 dilution), were applied to the tissues. A ready-to-use biotinylated secondary antibody was applied to bind the primary antibody. A streptavidin-peroxidase conjugate was applied to the same tissue slide as shown in FIG. 6 (HistoST5050 detection kit, ZYMED™ Laboratories Inc.). The presence of peroxidase was revealed by addition of 3,3'-diaminobenzidine tetrahydrochloride solution for color reaction as described in Chen et al [Chen Y M, et al. 1998].

TABLE 2A

| | Rates of positive staining | |
|---|---|---|
| Antibody[a] | Tumorous tissue | Non-tumorous tissues |
| GRL1 | 0% (0/9) | 38.5% (5/13) |
| GRL7 | 6.3% (1/16) | 61.5% (8/13) |
| Total | 4.0%(1/25) | 50% (13/26) |

TABLE 2B

| | No. of cases in the tissue pairs with different GNMT staining[a] | | | | |
|---|---|---|---|---|---|
| Antibody[a] | N+/T+ | N+/T− | N−/T+ | N−/T− | Total pairs |
| GRL1 | 0 | 3 | 0 | 4 | 7 |
| GRL7 | 1 | 3 | 0 | 5 | 9 |
| Total | 1 | 6 | 0 | 9 | 16 |

[a]The dilutions for mAbs GRL1 and GRL7 (ascites) were 1:100 and 1:25, respectively.

3.3. Establishment of Serum and Plasma GNMT Quantitative EIA 3.3.1 Patients and Normal Serum A total of 545 sera or plasma samples from Taipei Municipal Jen—Ai hospital were collected in our laboratory between August 2000 and February 2002, 413 from healthy people, 90 from chronic hepatitis patients who had viral hepatitis, 20 from patients who were diagnosed as liver cirrhosis by pathological method, and 22 from HCC patients who were confirmed by physical, ultrasonic and pathological methods.

3.3.2. GNMT Quantitative Enzyme immunoassay (EIA)

GNMT concentrations in human serum or plasma were measured by an indirect EIA method. Briefly, ninety-six well plates (COSTAR™ 3590 96 well assay plate, Corning, N.Y., USA) were coated with ammonium sulfate precipitated rabbit serum anti-GNMT (R4) 0.1 µl/well (concentration 7.13 mg/ml) in 0.02 M sodium carbonate buffer (pH 9.6) for 1 hour at 37° C. The wells were post-coated with 5% skim milk in TBS (50 mM Tris, 0.14 M NaCl) at 37° C. for 2 hours. The standards and samples were in a sample diluent (TBS with 0.05% TWEEN-20™ and 1% BSA). The plates were put into a two-fold dilution of standard from 500 ng/ml to 7.8 ng/ml and two-fold dilution of serum samples at 37° C. for 1 hour. The Goat anti-mouse peroxidase 1: Tweenm-20 3000 dilution was added to the well plate at 37° C. for 1 hour. After washing, OPD was added and a wait of 30 min at RT was made. The reaction was stopped by adding 100 µl 3M $H_2SO_4$. The absorption was read at 490 nm by EIA reader, BIOTEK™ Elx808. The results of standards were calculated by the 2-parameter logistic curve fit method, and extrapolated to the concentration of serum samples.

3.3.3. Statistic Analysis

Figure 7A:
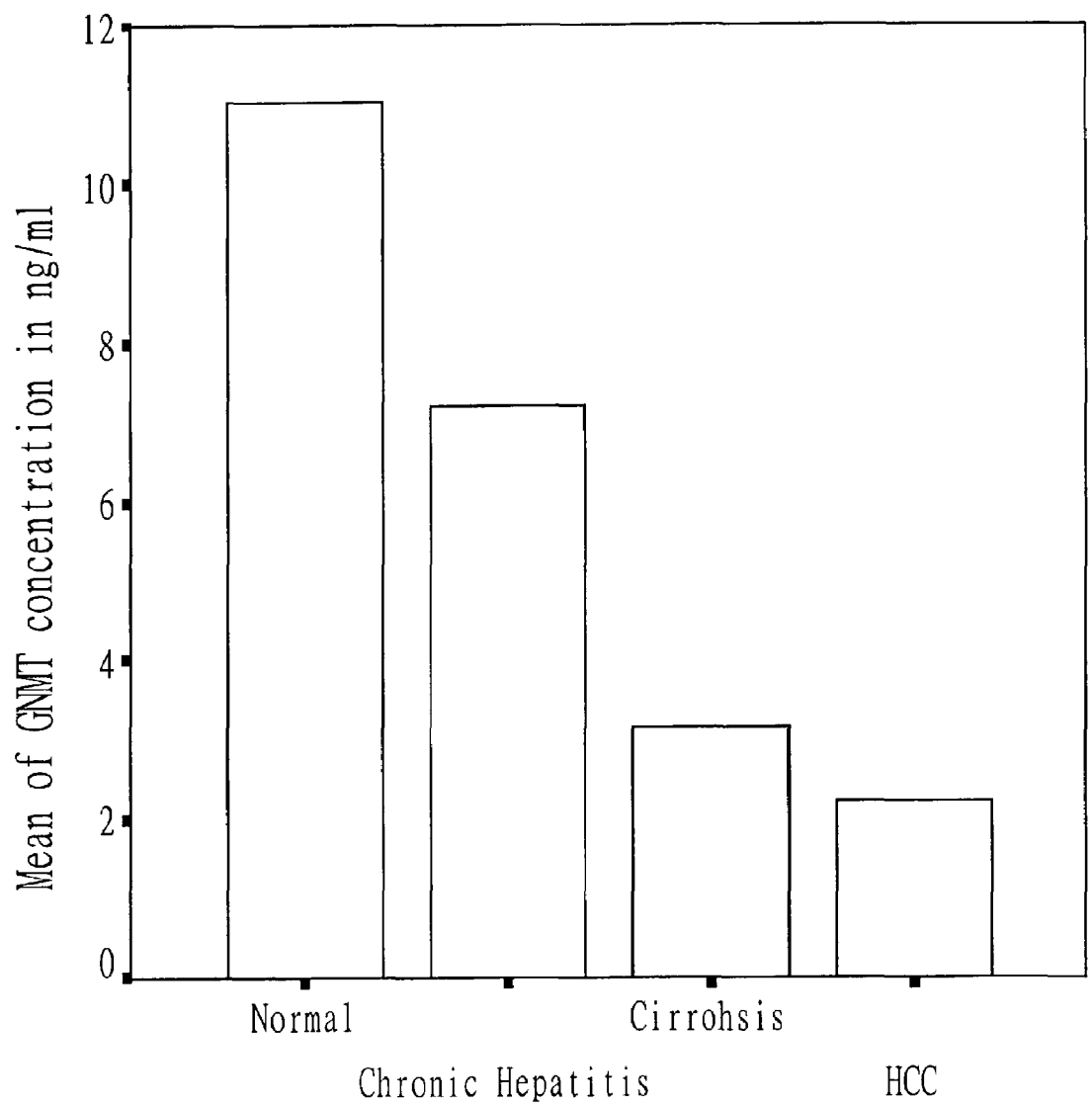
FIG. 7A–7B are the mean plot and box plot for the distribution of the results from GNMT quantitative Enzyme immunoassay. Total 545 sera samples included 413 healthy sera from health checking people in Jen-I hospital, 90 chronic hepatitis patients, 20 confirmed cirrhosis patient and 22 HCC patients were collected in our laboratory. In the preliminary screening of these sera, the mean and standard deviation of normal people, patients with chronic hepatitis, cirrhosis, HCC were 11.04±16.24, 7.19±9.25, 3.14±3.38, 2.19±2.54 ng/ml respectively.
Figure 7B:
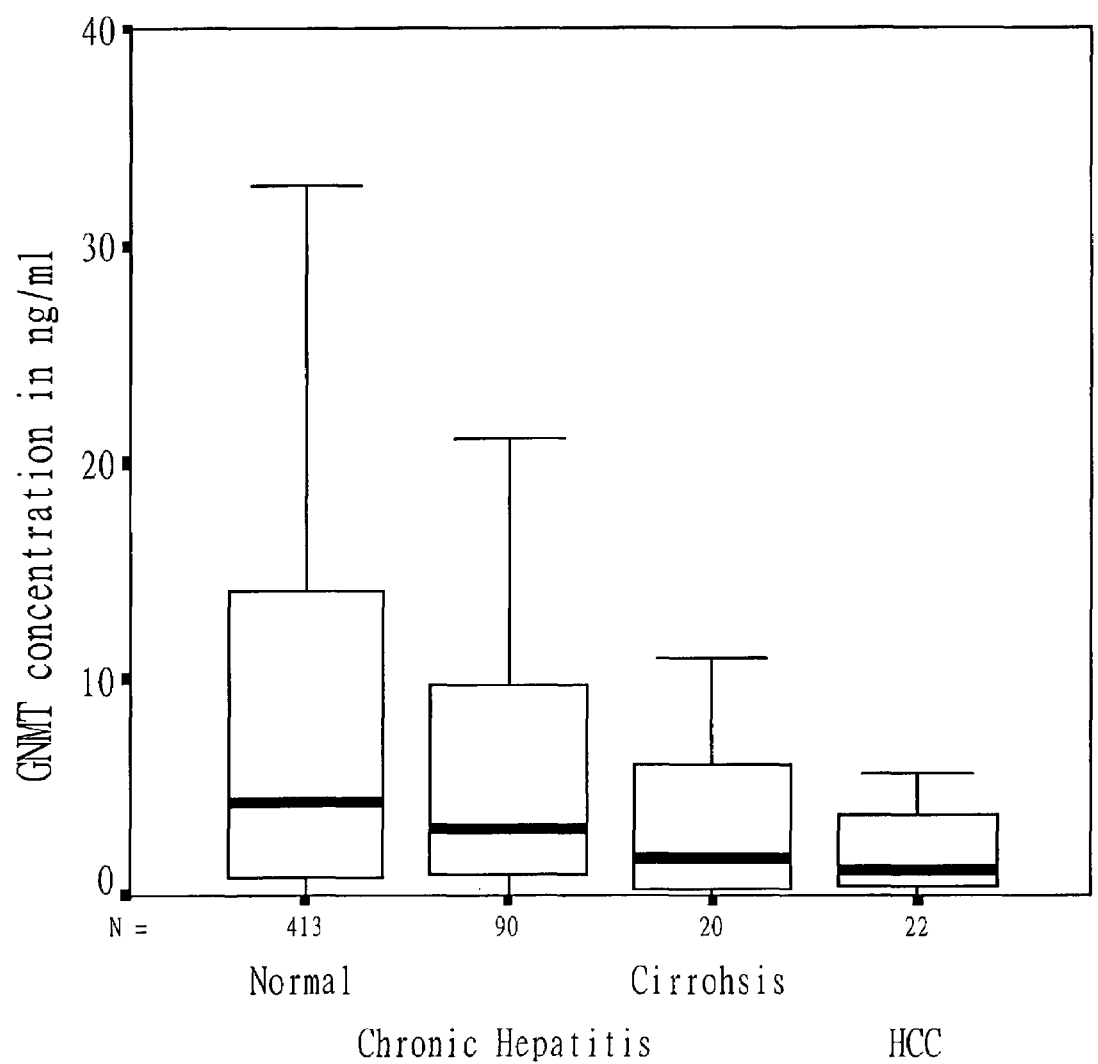

Statistical analyses were performed using the SPSS™ statistical software (SPSS™ Inc. Chicago, Ill.). One-way ANOVA was performed to determine statistical significance among the differences of GNMT protein concentrations in sera among the 4 groups: normal, patients with chronic hepatitis, cirrhosis, HCC. A post hoc test was used, when the p value was near 0.5, and LSD was used to demonstrate significance between the groups shown in FIG. 7.

REFERENCES

1. Aden D P, Fogel H, Plotkin S, Damjanov I, Knowles B B. Nature 282:615–616; 1979
2. Bork P, Ouzounis C, Sander C, Scharf M, Schneider R, Sonnhammer E. Protein Sci 1: 1677–1690; 1992.
3. Chang C, Lin Y, O-Lee T, Chou C, Lee T, Liu T, P'Eng F, Chen T, Hu C. Mol Cell Biol 3:1133–1137; 1983.
4. Chen S Y, Wong F H, Lin J R, Liu T Y, Lin C H, Lin P P, Hsieh J T, Chen Y M. Functional characterization of a putative tumor susceptibility gene-GNMT in the Benzo[a]pyrene- detoxification pathway. (submitted)
5. Chen Y M, Hu C P, Chen P H, Chu M H, Tsai Y T, Lee S D, Chang C M. Hepatology 8:547–552; 1988.
6. Chen Y M, Shiu J Y, Tzeng S J, Shih L S, Chen Y J, Lui W Y, Chen P H. Int J Cancer 75:787–793; 1998.
7. Chen Y M, Chen L Y, Wong F H, Lee C M, Chang T J, Yang-Feng T L. Genomics 66:43–47; 2000.
8. Chen Y M, Zhang X Q, Dahl C E, Samuel K P, Schooley R T, Essex M, Papas T S. J Immunol 147:2368–2376; 1991.
9. Chu T M, Kawinsky E, Lin T H. Hybridoma 12:417–429; 1993.
10. Cook R J, Wagner C. Proc Natl Acad Sci USA 81:3631–3634; 1984.
11. Cortese R, Monaci P, Luzzago A, Santini C, Bartoli F, Cortese I, Fortugno P, Galfre G, Nicosia A, Felici F. Curr Opin Biotech 7:616–621; 1996.
12. Fogh J, Trempe G. In: Fogh J. eds Human tumor cell in vitro. New York, Plenum, 115–119; 1976.
13. Fogh J, Wright W C, Loveless J D. J nat Cancer Inst 41:209–214; 1977.
14. Guan K L, Dixon J E. Anal Biochem 192:262–267; 1991.
15. Heady J E, Kerr S J. Cancer Res 35:640–3; 1975.
16. Houser W H, Hines R N, Bresnick E. Biochemistry 24:7839–7845; 1985.
17. Javitt N B. FASEB J 4:161–168; 1990.
18. Kerr S J. J Biol Chem 247: 4248–4252; 1972.
19. Krupenko N I, Wagner C. J Biol Chem 272:27140–27146; 1997.
20. Lai M C, Yang D R, Chuang M J. Appl Environ Microbiol 65:828–33; 1999a.
21. Lai M C, Yang D R, Chuang M J. Annu Meet Am Soc Microbiol (Abstract I17), Washington, D.C; 1999b.
22. Luka Z, Cerone R, III Phillips J A, Mudd H S, Wagner C. Hum Genet 110:68–74; 2002.
23. Morgan C L, Newman D J, Burrin J M, Price C P. J Immunol Methods 217: 51–60; 1998.
24. Mudd S H, Cerone R, Schiaffino M C, Fantasia A R, Minniti G, Caruso U, Lorini R, Watkins D, Matiaszuk N, Rosenblatt D S, Schwahn B, Rozen R, LeGros L, Kotb M, Capdevila A, Luka Z, Finkelstein J D, Tangerman A, Stabler S P, Allen R H, Wagner C. J Inherit Metab Dis 24: 448–64; 2001.
25. Nakabayashi H, Taketa K, Miyano K, Yamane T, Sato J. Cancer Res 42:3858–3862; 1982.
26. Ogawa H, Fujioka M. J Biol Chem 257:3447–3452; 1982.
27. Ogawa H, Gom T, Fujioka M. Comp Biochem Phys B 106: 601–611; 1993.
28. Ogawa H, Gomi T, Takusagawa F, Fujioka M. Int J Biochem Cell B 30:13–26; 1998.
29. Raha A, Wagner C, MacDonald R G, Bresnick E. J Biol Chem 269:5750–5756; 1994.
30. Tseng T L, Shih Y P, Huang Y C, Wang C K, Chen P H, Chang J G, Yeh K T, Struewing J P, Chen Y M, Buetow K H. Genotypic and Phenotypic Characterization of a Putative Tumor Susceptibility Gene, GNMT, in Liver Cancer (submitted).
31. Zhang Y J, Chen C J, Haghighi B, Yang G Y, Hsieh L L, Wang L W, Santella R M. Cancer Res 51:1720–1725; 1991.

---

What is claimed is:

1. A monoclonal antibody that binds glycine N-methyltransferase, said monoclonal antibody produced by hybridoma cell line GRL7, which is deposited under ATCC Deposit Designation PTA-5195.

2. A monoclonal antibody that binds glycine N-methyltransferase, said monoclonal antibody produced by hybridoma cell line GRL1, which is deposited under ATCC Deposit Designation PTA-5319.

* * * * *